(12) United States Patent
Nishimura et al.

(10) Patent No.: US 8,363,901 B2
(45) Date of Patent: Jan. 29, 2013

(54) RADIOGRAPHIC TOMOGRAPHY APPARATUS

(75) Inventors: Tomoyoshi Nishimura, Tokyo (JP); Jun Enomoto, Kanagawa-ken (JP); Hirofumi Sawada, Minami-ashigara (JP); Sadato Akahori, Odawara (JP); Eiichi Kanagawa, Minami-ashigara (JP); Yasunori Ohta, Yokohama (JP); Noriaki Ida, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 631 days.

(21) Appl. No.: 12/591,107

(22) Filed: Nov. 9, 2009

(65) Prior Publication Data

US 2010/0119116 A1     May 13, 2010

(30) Foreign Application Priority Data

Nov. 13, 2008   (JP) .................................. 2008-290761

(51) Int. Cl.
*G06K 9/00* (2006.01)
(52) U.S. Cl. ....................................... 382/107; 382/131
(58) Field of Classification Search .................. 382/107, 382/128, 131, 132; 600/413, 427; 378/8, 378/20, 95
See application file for complete search history.

(56) References Cited

U.S. PATENT DOCUMENTS

| | | | |
|---|---|---|---|
| 7,127,028 B2 | 10/2006 | Sendai | 378/21 |
| 7,327,823 B2 * | 2/2008 | Matsuura | 378/8 |
| 2003/0225325 A1 * | 12/2003 | Kagermeier et al. | 600/407 |
| 2006/0074300 A1 | 4/2006 | Green | 600/427 |
| 2006/0235295 A1 | 10/2006 | Boese et al. | 600/428 |
| 2010/0329514 A1 * | 12/2010 | Mundry | 382/107 |

* cited by examiner

*Primary Examiner* — Andrew W Johns
(74) *Attorney, Agent, or Firm* — Jean C. Edwards, Esq.; Edwards Neils PLLC

(57) ABSTRACT

A radiographic tomography apparatus includes a tomosynthetic image capturing section for applying radiation from a radiation source to an examinee at a plurality of different angles, and detecting the radiation transmitted through the examinee with a radiation conversion panel to capture a plurality of tomosynthetic tomography images of the examinee. The radiographic tomography apparatus further includes a still image capturing section for capturing a plurality of still images of the examinee in one image capturing position at different times, and a body motion detector for detecting a body motion of the examinee based on the still images captured by the still image capturing section.

10 Claims, 4 Drawing Sheets

RADIOGRAPHIC TOMOGRAPHY APPARATUS

CROSS-REFERENCE TO RELATED APPLICATION

This application is based upon and claims the benefit of priority from Patent Application No. 2008-290761 filed on Nov. 13, 2008, in the Japan Patent Office, of which the contents are incorporated herein by reference.

BACKGROUND OF THE INVENTION

1. Field of the Invention

The present invention relates to a radiographic tomography apparatus, which is capable of detecting body motion of an examinee, particularly in cases where the examinee should be kept still while a radiographic image of the examinee is being captured.

2. Description of the Related Art

In a radiographic imaging process, a satisfactory radiographic image of an examinee may not be captured if the body of the examinee moves too much, or if the region of the examinee that is to be imaged significantly changes in position. There have been proposed radiographic tomography apparatus, which are designed to reduce the effect that body motions of the examinee have on a radiographic image (see U.S. Patent Application Publication No. 2006/0074300 A1, and U.S. Patent Application Publication No. 2006/0235295 A1).

According to U.S. Patent Application Publication No. 2006/0074300 A1, electrodes are attached to the chest of a patient (see paragraph [0020] of U.S. Patent Application Publication No. 2006/0074300 A1), and a radiographic image of the patient is enlarged or reduced, depending on the breathing characteristic of the patient corresponding to impedance changes detected through the electrodes, thereby reducing image blurs (see paragraph [0024] of U.S. Patent Application Publication No. 2006/0074300 A1).

According to U.S. Patent Application Publication No. 2006/0235295 A1, an ECG probe is attached to a patient (see paragraph [0025] of U.S. Patent Application Publication No. 2006/0235295 A1), whereby the motion of the heart of the patient is calculated from a CT image of the patient, and a PET image or the like of the patient is corrected based on the calculated motion (see paragraph [0028] of U.S. Patent Application Publication No. 2006/0235295 A1).

There has also been proposed a radiographic tomography apparatus using tomosynthesis for acquiring three-dimensional image information in one tomographic imaging process (see U.S. Pat. No. 7,127,028 B2). The radiographic tomography apparatus disclosed in U.S. Patent Application Publication No. 2006/0074300 A1 and U.S. Patent Application Publication No. 2006/0235295 A1 detect only body motions caused by heart beating and breathing, but do not take into account other body motions of the patient. As a result, if the patient produces body motions other than body motions caused by the patient's heart beat and breathing, then the measurement accuracy of the radiographic tomography apparatus tends to be lowered. U.S. Pat. No. 7,127,028 B2, however, also fails to reveal anything concerning such other body motions.

SUMMARY OF THE INVENTION

It is an object of the present invention to provide a radiographic tomography apparatus having increased measurement accuracy.

A radiographic tomography apparatus according to the present invention includes a tomosynthetic image capturing section for applying radiation from a radiation source to an examinee at a plurality of different angles, and detecting the radiation transmitted through the examinee with a radiation conversion panel to capture a plurality of tomosynthetic tomography images of the examinee. The radiographic tomography apparatus further includes a still image capturing section for capturing a plurality of still images of the examinee in one image capturing position at different times, and a body motion detector for detecting a body motion of the examinee based on the still images captured by the still image capturing section.

With the above arrangement, a body motion of the examinee is detected based on still images captured at one image capturing position at different times. Therefore, it is possible to determine the reliability of the tomosynthetic tomography images acquired by the tomosynthetic image capturing section, based on the body motion detected by the body motion detector. As a result, the measurement accuracy of the radiographic tomography apparatus can be increased.

The still images may be any still images which enable a body motion of the examinee to be determined. For example, the still images may be images generated by a digital camera, tomosynthetic tomography images, or simple X-ray images.

The radiographic tomography apparatus may further include a body motion indicator for indicating a body motion of the examinee, which is detected by the body motion detector, when the body motion is large enough to prevent a sufficient level of accuracy from being attained when capturing tomosynthetic tomography images of the examinee. Therefore, the user of the radiographic tomography apparatus, e.g., a doctor, a radiographic technician, or the like, can easily recognize body motion when the body motion is indicated by the body motion indicator.

The still image capturing section may capture still images respectively immediately before and after the tomosynthetic image capturing section captures the tomosynthetic tomography images of the examinee. Alternatively, the still images may be captured at one position during forward and backward strokes of the radiation source while one tomosynthetic image is being captured. If the still images comprise tomosynthetic tomography images, then since the tomosynthetic tomography images are available to perform tomosynthesis, and can detect body motions of the examinee, the radiographic tomography apparatus serves as a space saver. If the still images comprise simple X-ray images captured when the radiation source applies radiation at an increased dose, then since the tomosynthetic image capturing section can capture both tomosynthetic images and still images (simple X-ray images), the radiographic tomography apparatus also serves as a space saver.

The still images may comprise still images captured in a direction perpendicular to a recumbent surface of an imaging bed on which the examinee lies.

The body motion detector may detect body motion based on a difference between the still images. Specifically, the body motion detector may extract respective contours of the still images, and detect the body motion of the examinee based on a difference between the contours.

The radiographic tomography apparatus may further include a display unit, and an input unit for entering an image recapturing request from the user. The body motion detector may detect a body motion distance of the examinee based on the still images, and the display unit may display the body motion distance detected by the body motion detector. Then, when the image recapturing request is entered into the input unit, the tomosynthetic image capturing section may capture a plurality of tomosynthetic tomography images of the examinee again. With this arrangement, it is easy to confirm whether image recapturing is required or not, and if so, to perform the tomosynthetic image capturing process again.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
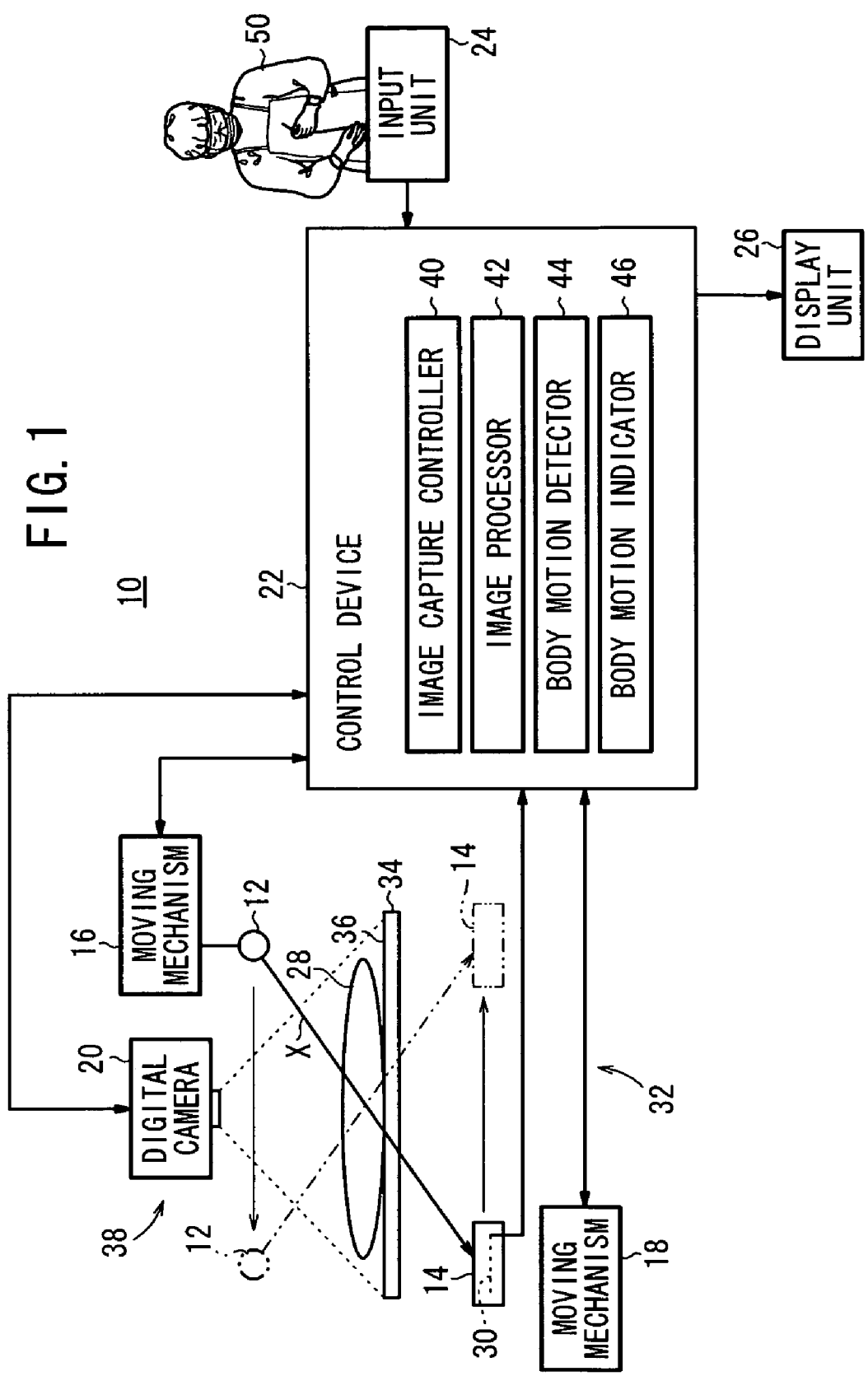
FIG. 1 is a block diagram of a radiographic tomography apparatus according to a first embodiment of the present invention.

Like or corresponding components are denoted using like or corresponding reference characters throughout the views.

Radiographic tomography apparatus according to preferred embodiments of the present invention will be described in detail below with reference to FIGS. 1 through 4.

A. First Embodiment

1. Configuration of Radiographic Tomography Apparatus 10

FIG. 1 shows in block form a radiographic tomography apparatus 10 according to a first embodiment of the present invention. As shown in FIG. 1, the radiographic tomography apparatus 10 comprises a radiation source 12, a cassette 14, a first moving mechanism 16, a second moving mechanism 18, a digital camera 20, a control device 22, an input unit 24, and a display unit 26.

The radiation source 12 emits a given radiation X, such as X-rays or the like, at a given dose in response to a command from the control device 22. The cassette 14 houses therein a radiation conversion panel 30, which detects the radiation X emitted from the radiation source 12 and transmitted through an examinee (patient) 28, and converts the detected radiation X into radiographic image information. The radiation conversion panel 30 outputs the radiographic image information to the control device 22. The first moving mechanism 16 moves the radiation source 12 in horizontal directions, as shown in FIG. 1, in response to a command from the control device 22. The second moving mechanism 18 moves the cassette 14 in the horizontal directions in response to a command from the control device 22. The radiation source 12, the radiation conversion panel 30, the first moving mechanism 16, the second moving mechanism 18, and the control device 22 collectively make up a tomosynthetic image capturing section 32.

The digital camera 20 captures a still image of the examinee 28, who lies on an upper recumbent surface 36 of an imaging bed 34, in response to a command from the control device 22. In the first embodiment, the digital camera 20, which is fixedly disposed above the imaging bed 34, has an imaging direction thereof disposed perpendicular to the upper recumbent surface 36 of the imaging bed 34, and is positioned in vertical alignment with the center of the imaging bed 34 in the transverse directions, i.e., horizontal directions parallel the to imaging bed 34 in FIG. 1. The digital camera 20 and the control device 22 jointly make up a still image capturing section 38 according to the first embodiment.

The control device 22 comprises an image capture controller 40, an image processor 42, a body motion detector 44, and a body motion indicator 46.

The image capture controller 40 controls the tomosynthetic image capturing section 32 in order to perform a tomosynthetic image capturing process, and also controls the still image capturing section 38 in order to perform a still image capturing process.

More specifically, in the tomosynthetic image capturing process, the image capture controller 40 controls the first moving mechanism 16 and the second moving mechanism 18 so as to move the radiation source 12 and the radiation conversion panel 30, one on each side of the examinee 28, synchronously in mutually opposite horizontal directions, such that a line interconnecting the center of the radiation source 12 and the center of the radiation conversion panel 30 is held substantially in alignment with the direction along which the radiation source 12 emits radiation X. When the radiation source 12 and the radiation conversion panel 30 are moved synchronously in this manner, the image capture controller 40 also controls the radiation source 12 to emit radiation X, and reads radiographic image information (tomosynthetic tomography image data) acquired by the radiation conversion panel 30.

In the still image capturing process, the image capture controller 40 controls the digital camera 20 in order to capture a still image (appearance image) of the examinee 28, and reads the still image data captured by the digital camera 20.

The image processor 42 processes the tomosynthetic tomography image data, which have been read from the radiation conversion panel 30 by the image capture controller 40. More specifically, the image processor 42 processes a plurality of tomosynthetic tomography image data, which are acquired each time that the radiation source 12 emits radiation X, according to both a shift-and-add process and a filtered-back projection process, thereby producing a tomographic image (reconstructed tomographic image) at any desired image plane position (slice height). The image processor 42 then performs various image correcting processes, which may include gain adjustment (sensitivity correction), offset adjustment (gradation correction), edge emphasis (frequency emphasis), etc., on the reconstructed tomographic image. Thereafter, the image processor 42 displays the reconstructed tomographic image on the display unit 26.

The body motion detector 44 detects an abnormal body motion of the examinee 28 based on the still image data, which have been read from the digital camera 20 by the image capture controller 40. More specifically, the body motion detector 44 determines whether or not the examinee 28 has produced an abnormal body motion during the tomosynthetic image capturing process, based on data of two still images acquired by the digital camera 20, as shall be described in detail later. An abnormal body motion refers to a body motion that is large enough to prevent a sufficient level of accuracy from being attained during the tomosynthetic image capturing process.

When the body motion detector 44 detects an abnormal body motion, the body motion indicator 46 displays an announcement, so as to indicate the abnormal body motion on the display unit 26.

The image capture controller 40, the image processor 42, the body motion detector 44, and the body motion indicator 46 are implemented by a CPU (Central Processing Unit), a memory, etc., which are not illustrated.

The input unit 24 is a device for entering commands from a doctor 50 concerning the tomosynthetic image capturing process. The input unit 24 comprises operation buttons, a keyboard, a mouse, etc., for example.

The display unit 26 displays images based on output signals from the control device 22.

The basic arrangements required to perform the tomosynthetic image capturing process may be similar to those disclosed in U.S. Pat. No. 7,127,028 B2, the full disclosure of which is expressly incorporated herein by reference.

2. Sequence for Tomosynthetic Image Capturing Process

Figure 2:
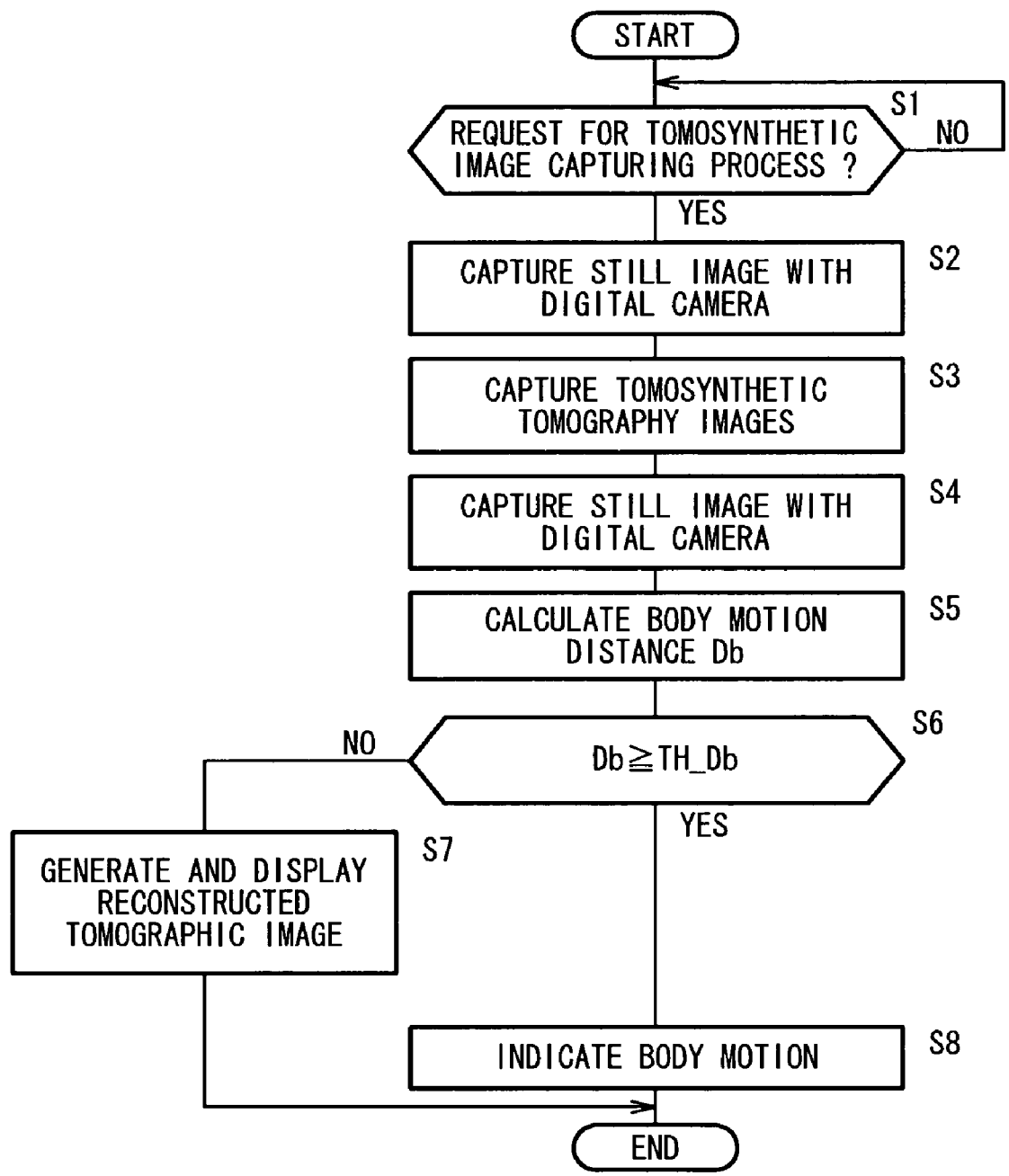
FIG. 2 is a flowchart of a sequence for carrying out a tomosynthetic image capturing process with the radiographic tomography apparatus according to the first embodiment.

A sequence for performing a tomosynthetic image capturing process using the radiographic tomography apparatus 10 according to the first embodiment, while the examinee 28 is monitored for body motions, will be described below with reference to FIG. 2. FIG. 2 shows a flowchart of such a sequence for performing a tomosynthetic image capturing process using the radiographic tomography apparatus 10 according to the first embodiment.

In step S1 shown in FIG. 2, the control device 22 determines whether or not the doctor 50 has entered a request for a tomosynthetic image capturing process into the input unit 24'. If the doctor 50 has not entered a request for a tomosynthetic image capturing process into the input unit 24 (S1: NO), then the control device 22 continues to check whether such a request has been made in step S1. If the doctor 50 has entered a request for a tomosynthetic image capturing process into the input unit 24 (S1: YES), then the control device 22 sends a command to capture a still image to the digital camera 20 in step S2. In response to this command, the digital camera 20 captures a still image (appearance image) of the examinee 28.

In step S3, the control device 22 carries out the tomosynthetic image capturing process. More specifically, the control device 22 controls the first moving mechanism 16 and the second moving mechanism 18, so as to move the radiation source 12 and the radiation conversion panel 30, one on each side of the examinee 28, synchronously in mutually opposite horizontal directions. At the same time, the control device 22 controls the radiation source 12 to emit radiation X. Therefore, the radiation X, which is emitted from the radiation source 12, is applied to the examinee 28 at different angles while the radiation source 12 and the radiation conversion panel 30 move synchronously in mutually opposite horizontal directions. The radiation conversion panel 30 detects radiation X transmitted through the examinee 28, and converts the detected radiation X into radiographic image information (tomosynthetic tomography image data).

When the tomosynthetic image capturing process is completed and all necessary radiographic image information has been acquired, in step S4, the control device 22 sends a command again to the digital camera 20 in order to capture a still image. In response to the second command, the digital camera 20 captures a second still image of the examinee 28.

In step S5, the control device 22 calculates a body motion distance Db [mm] of the examinee 28 based on the two still images, one captured immediately before the tomosynthetic image capturing process, and one captured immediately after the tomosynthetic image capturing process. The body motion distance Db is defined, for example, as a difference between two contours, which are extracted from the two still images.

In step S6, the control device 22 determines whether or not the calculated body motion distance Db is equal to or greater than a given body motion distance threshold TH_Db [mm]. The body motion distance threshold TH_Db represents, for example, a maximum value of body motion that is capable of maintaining a level of accuracy, which is required to reliably capture a plurality of tomosynthetic tomography images. If the body motion distance Db is smaller than the body motion distance threshold TH_Db (S6: NO), then the control device 22 judges that the examinee 28 has not produced a body motion (abnormal body motion) large enough to require image recapturing by the tomosynthetic image capturing process. Thereafter, the control device 22 completes the entire image capturing process (the tomosynthetic image capturing process and the still image capturing process), and displays, in step S7, a reconstructed tomographic image based on a plurality of tomosynthetic tomography image data on the display unit 26. If the body motion distance Db is equal to or greater than the body motion distance threshold TH_Db (S6: YES), then the control device 22 judges that the examinee 28 has produced an abnormal body motion during the tomosynthetic image capturing process. Then, in step S8, the control device 22 displays an announcement concerning the abnormal body motion on the display unit 26. Upon seeing the displayed announcement, the doctor 50 can enter a request into the input unit 24, for another tomosynthetic image capturing process to be carried out to recapture the radiographic image information. An abnormal body motion implies that the examinee 28, who normally should remain motionless, has actually moved a distance ranging from several mm to several tens of mm, for example.

3. Advantages of the First Embodiment

According to the first embodiment, as described above, the body motion detector 44 detects a body motion of the examinee 28 based on two still images of the examinee captured by the fixed digital camera 20 in one image capturing position, which are captured immediately before and after the tomosynthetic image capturing process. Therefore, it is possible to determine the reliability of the tomosynthetic tomography images acquired by the tomosynthetic image capturing section 32, based on body motions detected by the body motion detector 44. As a result, measurement accuracy of the radiographic tomography apparatus 10 can be increased.

According to the first embodiment, when the examinee 28 produces an abnormal body motion, the body motion indicator 46 of the control device 22 displays an announcement concerning the abnormal body motion on the display unit 26. Therefore, the radiographic tomography apparatus 10 can easily notify the doctor 50 of any abnormal body motions.

B. Second Embodiment

1. Differences from the First Embodiment

Figure 3:
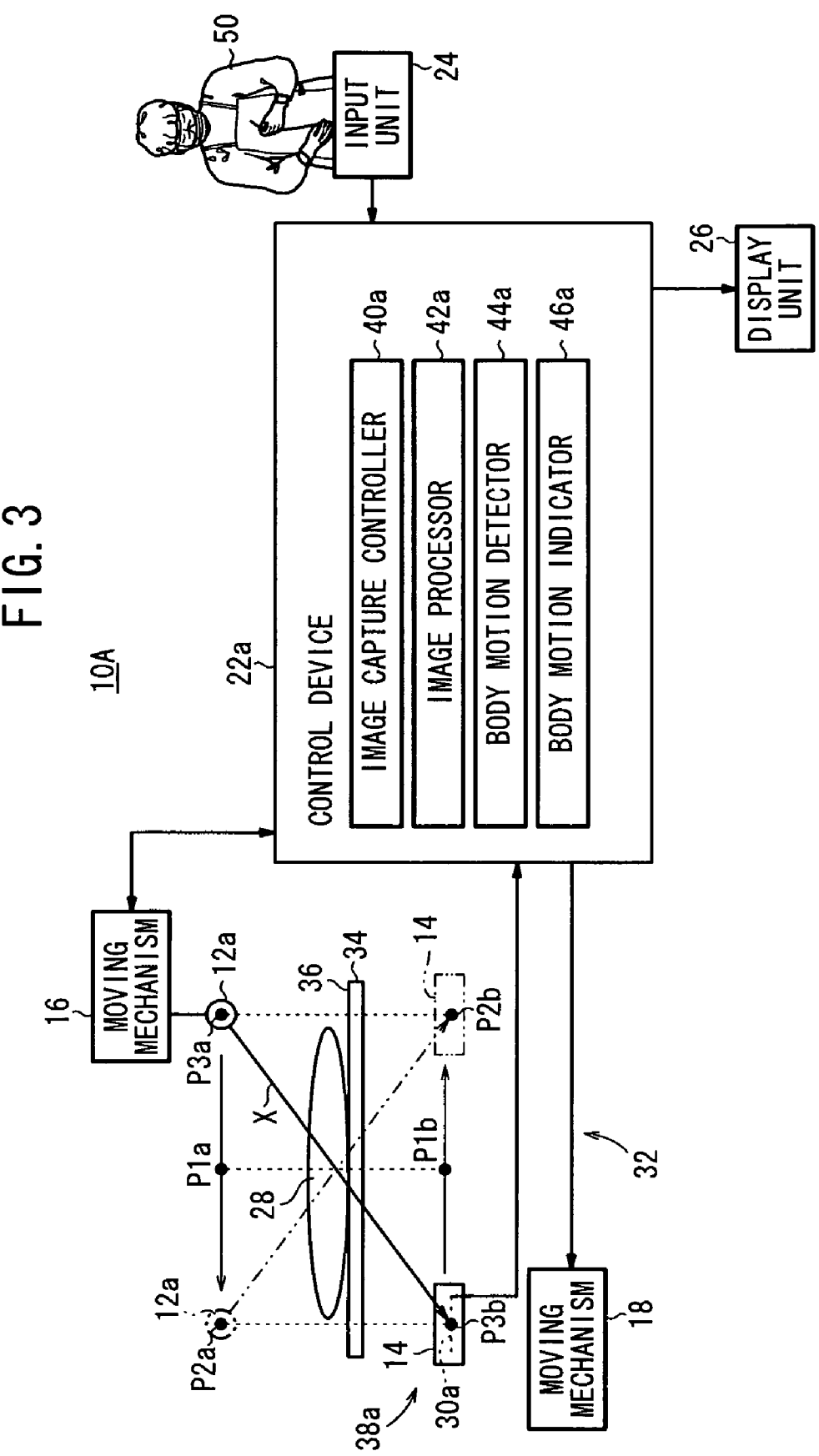
FIG. 3 is a block diagram of a radiographic tomography apparatus according to a second embodiment of the present invention.

FIG. 3 shows in block form a radiographic tomography apparatus 10A according to a second embodiment of the present invention. As shown in FIG. 3, the radiographic tomography apparatus 10A does not include the digital camera 20 of the radiographic tomography apparatus 10 according to the first embodiment. The radiographic tomography apparatus 10A includes a radiation source 12a, a radiation conversion panel 30a, and a control device 22a. The control device 22a comprises an image capture controller 40a, an image processor 42a, a body motion detector 44a, and a body motion indicator 46a. Still images of the examinee 28 can be captured by the radiation source 12a and the radiation conversion panel 30a. According to the second embodiment, the radiation source 12a, the radiation conversion panel 30a, and the image capture controller 40a collectively make up a still image capturing section 38a. The still image capturing section 38a can perform a simple X-ray image capturing process in order to acquire simple X-ray image data, which will be displayed directly, instead of being processed into a reconstructed image. Since the tomosynthetic tomography image is reconstructed from a plurality of tomosynthetic tomography image data, the dose of radiation X, which is applied in order to acquire the data of one tomosynthetic tomography image, may be smaller than the dose of the radiation X that is applied in order to acquire data of one simple X-ray image.

The radiation source 12a according to the second embodiment is able to emit radiation X at a dose required for the tomosynthetic image capturing process, and also is capable of emitting radiation X at a dose required for carrying out a simple X-ray image capturing process, which is greater than the dose required for the tomosynthetic image capturing process. The radiation conversion panel 30a is capable of detecting radiation X at a proper dose required for the tomosynthetic image capturing process, and also of detecting radiation X at a proper dose required for the simple X-ray image capturing process. Consequently, the radiation source 12a and the radiation conversion panel 30a in combination can acquire a tomosynthetic tomography image using a relatively small dose, and also can acquire a simple X-ray image that requires a relatively large dose. The image processor 42a can process both tomosynthetic tomography images as well as simple X-ray images.

2. Sequence for Tomosynthetic Image Capturing Process

Figure 4:
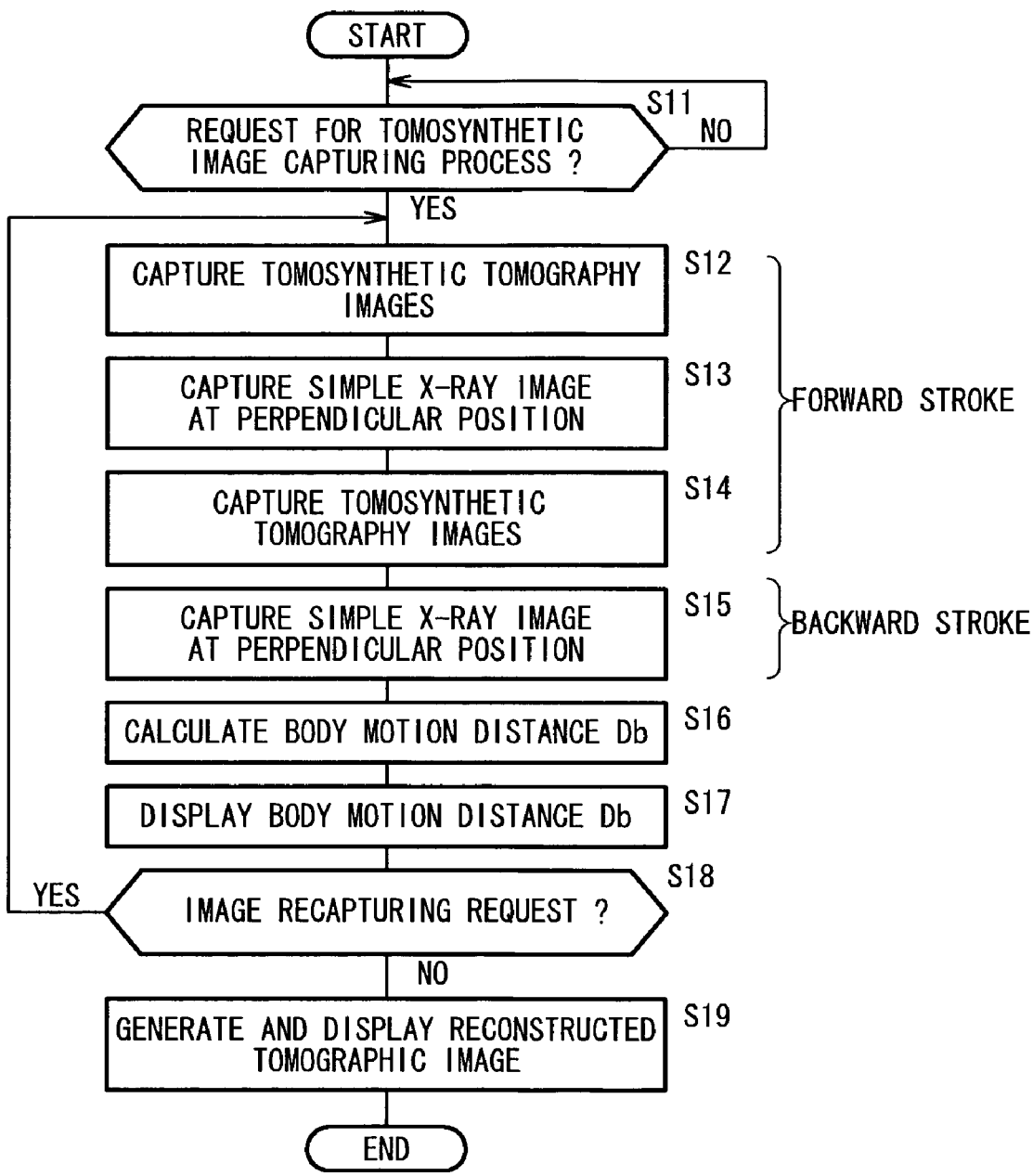
FIG. 4 is a flowchart of a sequence for carrying out a tomosynthetic image capturing process with the radiographic tomography apparatus according to the second embodiment.

A sequence for performing a tomosynthetic image capturing process using the radiographic tomography apparatus 10A according to the second embodiment, while the examinee 28 is monitored for body motions, will be described below with reference to FIG. 4. FIG. 4 shows a flowchart of such a sequence, for performing a tomosynthetic image capturing process using the radiographic tomography apparatus 10A according to the second embodiment.

In step S11, as shown in FIG. 4, the control device 22a determines whether or not the doctor 50 has entered a request for initiating the tomosynthetic image capturing process into the input unit 24. If the doctor 50 has not entered a request for a tomosynthetic image capturing process into the input unit 24 (S11: NO), then the control device 22a continues to check for such a request in step S11. If the doctor 50 has entered a request for a tomosynthetic image capturing process into the input unit 24 (S11: YES), the control device 22a starts to perform the tomosynthetic image capturing process in step S12. More specifically, the control device 22a controls the first moving mechanism 16 and the second moving mechanism 18, so as to move the radiation source 12a and the radiation conversion panel 30a, one on each side of the examinee 28, synchronously in mutually opposite horizontal directions from respective initial positions P3a, P3b. At the same time, the control device 22a controls the radiation source 12 to emit radiation X. The radiation conversion panel 30a detects radiation X transmitted through the examinee 28, and converts the detected radiation X into radiographic image information (tomosynthetic tomography image data).

During the tomosynthetic image capturing process, when the radiation source 12a reaches a position (perpendicular position P1a), which is disposed perpendicularly above the upper recumbent surface 36 of the imaging bed 34 and in vertical alignment with the center of the imaging bed 34, and the radiation conversion panel 30a reaches a corresponding position (perpendicular position P1b) disposed perpendicularly below the upper recumbent surface 36 of the imaging bed 34 in vertical alignment with the center of the imaging bed 34, the control device 22a increases the dose of radiation X emitted from the radiation source 12a, and performs a simple X-ray image capturing process in order to acquire data of a first simple X-ray image (still image) in step S13.

In step S14, the control device 22 resumes the tomosynthetic image capturing process. When the radiation source 12a and the radiation conversion panel 30a reach respective end positions P2a, P2b and the tomosynthetic image capturing process is completed, then the control device 22a controls the first moving mechanism 16 and the second moving mechanism 18 in order to move the radiation source 12a and the radiation conversion panel 30a synchronously and respectively toward the initial positions P3a, P3b. When the radiation source 12a and the radiation conversion panel 30a reach the respective perpendicular positions P1a, P1b, the control device 22a increases the dose of radiation X emitted from the radiation source 12a, and performs a simple X-ray image capturing process in order to acquire data of a second simple X-ray image (still image) in step S15.

In step S16, the control device 22a calculates a body motion distance Db [mm] of the examinee 28 based on the two simple X-ray images. The body motion distance Db is defined, for example, as a difference between two contours extracted from two simple X-ray images.

In step S17, the control device 22a displays, on the display unit 26, the calculated body motion distance Db together with an inquiry concerning whether image recapturing is required to be performed in the tomosynthetic image capturing process. If the doctor 50 enters a command indicating that image recapturing is not required into the input unit 24 (S18: NO), then the control device 22a completes the entire image capturing process (the tomosynthetic image capturing process and the simple X-ray image capturing process), and in step S19, displays on the display unit 26 a reconstructed tomographic image based on the plurality of tomosynthetic tomography image data. If the doctor 50 enters a command indicating that image recapturing is required into the input unit 24 (S18: YES), then control returns to step S12, so that the control device 22a carries out the tomosynthetic image capturing process once again.

3. Advantages of the Second Embodiment

The second embodiment offers the same advantages as the first embodiment. According to the second embodiment, in addition, the body motion distance Db is calculated based on two simple X-ray images, which are captured at the same position (perpendicular position P1a) in forward and backward strokes of the radiation source 12a during one tomosynthetic image capturing process. Since the tomosynthetic image capturing section 32a can perform both the tomosynthetic image capturing process as well as the simple X-ray image capturing process, and since no digital camera is required, the radiographic tomography apparatus 10A is more of a space saver, as compared with the radiographic tomography apparatus 10. Further, the accuracy with which body motions are detected is increased by use of simple X-ray images.

According to the second embodiment, when the control device 22a displays, on the display unit 26, the calculated body motion distance Db together with an inquiry concerning whether image recapturing is required to be performed in the tomosynthetic image capturing process, and the doctor 50 enters a command requiring image recapturing into the input unit 24, the tomosynthetic image capturing section 32a carries out the tomosynthetic image capturing process again. Consequently, it is easy to confirm whether image recapturing is required or not, and also to perform the tomosynthetic image capturing process again.

C. Modifications

The present invention is not limited to the above embodiments. Various changes and modifications may be made to the embodiments within the scope of the invention. Such changes and modifications will be described below.

In the first embodiment, the principles of the invention are applied to the radiographic tomography apparatus 10. In the second embodiment, the principles of the invention are applied to the radiographic tomography apparatus 10A. However, the principles of the invention also are applicable to other radiographic tomography apparatus.

In the first embodiment, when the body motion distance Db is equal to or greater than the body motion distance threshold TH_Db, the control device 22 displays an announcement concerning the abnormal body motion that occurred in the tomosynthetic image capturing process on the display unit 26. In the second embodiment, the control device 22 displays the calculated body motion distance Db, together with an inquiry concerning whether image recapturing is required to be preformed or not in the tomosynthetic image capturing process. However, the control device 22 may display different data in different ways on the display unit 26. For example, the control device 22 may display, on the display unit 26, both an announcement concerning the abnormal body motion, as well as an inquiry about whether image recapturing is required to be performed in the tomosynthetic image capturing process. The control device 22 may further display the announcement, the body motion distance Db, and/or the inquiry as audio information, rather than video information in the form of characters, images, etc.

In the first and second embodiments, a still image (an appearance image or a simple X-ray image) of the examinee 28 is captured by the digital camera 20, which has the imaging direction thereof oriented perpendicular to the upper recumbent surface 36 of the imaging bed 34, and is positioned in vertical alignment with the center of the imaging bed 34 in transverse directions, i.e., horizontal directions parallel to the imaging bed 34 as shown in FIG. 1. Alternatively, the still image is captured by the radiation source 12a and the radiation conversion panel 30a, when they are arranged in respective perpendicular positions P1a, P1b disposed perpendicularly above and below the upper recumbent surface 36 of the imaging bed 34 and in vertical alignment with the center of the imaging bed 34. However, the still image may be captured by the digital camera 20 or the radiation source 12a and the radiation conversion panel 30a, which may be disposed in any of various other desired positions and oriented in other desired directions. In the second embodiment, simple X-ray images are captured during the tomosynthetic image capturing process. However, simple X-ray images may be captured immediately before and after the tomosynthetic image capturing process. The tomosynthetic tomography image may be used as a still image.

In each of the first and second embodiments, the radiation source 12, 12a and the radiation conversion panel 30, 30a are moved synchronously in horizontal directions, i.e., in transverse directions across the imaging bed 34, as shown in FIGS. 1 and 3. However, the radiation source 12, 12a and the radiation conversion panel 30, 30a may be fixed to arcuate joint members, whereby the arcuate joint members are rotated to move the radiation source 12, 12a and the radiation conversion panel 30, 30a synchronously in mutually opposite directions.

In the first embodiment, a body motion of the examinee 28 is determined based on the body motion distance Db, which is defined as a difference between two contours extracted from two still images. In the second embodiment, a body motion of the examinee 28 is determined based on the body motion distance Db, which is defined as a difference between two contours extracted from two simple X-ray images. However, a body motion of the examinee 28 may be determined in other ways, insofar as the determination is based on two still images or two simple X-ray images. For example, if the difference between areas of two simple X-ray images, in which the density (luminance) thereof is equal to or greater than a predetermined value exceeds a predetermined threshold, then the examinee 28 may be judged to have produced an abnormal body motion.

In the second embodiment, a body motion of the examinee 28 is determined based on two simple X-ray images. However, a body motion of the examinee 28 may be determined based on two tomosynthetic tomography images.

Although certain preferred embodiments of the present invention have been shown and described in detail, it should be understood that various changes and modifications may be made to the embodiments without departing from the scope of the invention as set forth in the appended claims.

What is claimed is:

1. A radiographic tomography apparatus comprising:
   a tomosynthetic image capturing section for applying radiation from a radiation source to an examinee at a plurality of different angles, and detecting the radiation transmitted through the examinee with a radiation conversion panel to capture a plurality of tomosynthetic tomography images of the examinee;
   a still image capturing section for capturing a plurality of still images of the examinee in one image capturing position at different times; and
   a body motion detector for detecting a body motion of the examinee based on the still images captured by the still image capturing section
   wherein the still image capturing section comprises the radiation source and the radiation conversion panel, and the still images comprise tomosynthetic tomography images, and
   wherein the still images comprise tomosynthetic tomography images captured at one position in forward and backward strokes of the radiation source during one tomosynthetic image capturing process.

2. A radiographic tomography apparatus according to claim 1, further comprising:
   a body motion indicator for indicating a body motion of the examinee, which is detected by the body motion detector, when the body motion is large enough to prevent a sufficient level of accuracy from being attained when capturing the tomosynthetic tomography images of the examinee.

3. A radiographic tomography apparatus according to claim 1, wherein the still image capturing section comprises a digital camera.

4. A radiographic tomography apparatus according to claim 1, wherein the still image capturing section captures the still images respectively immediately before and after the tomosynthetic image capturing section captures the tomosynthetic tomography images of the examinee.

5. A radiographic tomography apparatus according to claim 1, wherein the body motion detector detects the body motion based on a difference between the still images.

6. A radiographic tomography apparatus according to claim 5, wherein the body motion detector extracts respective contours of the still images and detects the body motion of the examinee based on a difference between the contours.

7. A radiographic tomography apparatus according to claim 1, wherein the still images comprise still images captured in a direction perpendicular to a recumbent surface of an imaging bed on which the examinee lies.

8. A radiographic tomography apparatus according to claim 1, wherein the still images comprise simple X-ray images captured at one position in forward and backward strokes of the radiation source during one tomosynthetic image capturing process as the radiation source applies the radiation at an increased dose.

9. A radiographic tomography apparatus according to claim 8, wherein the still images comprise still images captured in a direction perpendicular to a recumbent surface of an imaging bed on which the examinee lies.

10. A radiographic tomography apparatus according to claim 1, further comprising:
a display unit; and
an input unit for entering an image recapturing request from a user,
wherein the body motion detector detects a body motion distance of the examinee based on the still images,
the display unit displays the body motion distance detected by the body motion detector, and
when the image recapturing request is entered into the input unit, the tomosynthetic image capturing section captures a plurality of tomosynthetic tomography images of the examinee again.

* * * * *